United States Patent
Chakarian et al.

(10) Patent No.: US 12,080,574 B2
(45) Date of Patent: Sep. 3, 2024

(54) LOW OPEN AREA AND COUPON ENDPOINT DETECTION

(71) Applicant: APPLIED MATERIALS, INC., Santa Clara, CA (US)

(72) Inventors: Varoujan Chakarian, San Jose, CA (US); Blake W Erickson, Gilroy, CA (US)

(73) Assignee: Applied Materials, Inc., Santa Clara, CA (US)

( * ) Notice: Subject to any disclaimer, the term of this patent is extended or adjusted under 35 U.S.C. 154(b) by 804 days.

(21) Appl. No.: 16/932,630

(22) Filed: Jul. 17, 2020

(65) Prior Publication Data
US 2022/0020617 A1    Jan. 20, 2022

(51) Int. Cl.
*H01L 21/67* (2006.01)
*G01J 3/02* (2006.01)
(Continued)

(52) U.S. Cl.
CPC ...... *H01L 21/67253* (2013.01); *G01J 3/0218* (2013.01); *G01J 3/32* (2013.01);
(Continued)

(58) Field of Classification Search
CPC .......... H01J 37/32981; H01J 37/32972; H01J 37/32963; H01J 2237/2445;
(Continued)

(56) References Cited

U.S. PATENT DOCUMENTS 5,097,430 A * 3/1992 Birang ............. H01J 37/32935
                                                    216/60
5,995,235 A    11/1999 Sui et al.
(Continued)

FOREIGN PATENT DOCUMENTS

WO    2005028705 A1    3/2005

OTHER PUBLICATIONS

PCT International Search Report and Written Opinion for International Application No. PCT/US2021/041858 mailed Nov. 11, 2021, 8 pages.

*Primary Examiner* — Yuechuan Yu
(74) *Attorney, Agent, or Firm* — Lowenstein Sandler LLP (57) ABSTRACT

The disclosure describes apparatus and method for detecting an endpoint in plasma-assisted wafer processing in a chamber. A fiber array comprising a plurality of fibers collects optical emission light from the chamber during the plasma-assisted wafer processing. The fiber array is split into two or more groups of fibers, each group carrying a portion of the light to a segment of a photodetector. Each segment of photodetector has a corresponding narrowband optical filter designed for a specific range of wavelengths. A computer processor analyzes detected signals from the plurality of segments of the photodetector, and determines, based on the analysis of the detected signals, an endpoint of the plasma-assisted wafer processing as indicated by the presence or the absence of the one or more chemical species in the chamber. The photodetector can be based on photomultiplier tube (PMT) array or based on photodiodes (e.g., avalanche photodiodes (APDs)).

16 Claims, 7 Drawing Sheets

(51) Int. Cl.
*G01J 3/32* (2006.01)
*G01J 3/36* (2006.01)
*G01N 33/00* (2006.01)
*H01J 37/32* (2006.01)
*H01L 21/66* (2006.01)

(52) U.S. Cl.
CPC ............ *G01J 3/36* (2013.01); *G01N 33/0009* (2013.01); *H01J 37/32963* (2013.01); *H01J 37/32972* (2013.01); *H01J 37/32981* (2013.01); *H01L 22/26* (2013.01); *H01J 2237/2445* (2013.01)

(58) Field of Classification Search
CPC ... G01N 33/0009; G01N 21/62; G01J 3/0218; G01J 3/32; G01J 3/36; G01J 2003/1213; H01L 21/67253; H01L 22/26
See application file for complete search history.

(56) References Cited

U.S. PATENT DOCUMENTS

| | | | |
|---|---|---|---|
| 2003/0029834 A1* | 2/2003 | Lill | H01J 37/32935 156/345.24 |
| 2003/0038112 A1* | 2/2003 | Liu | H01J 37/3299 216/60 |
| 2005/0009347 A1* | 1/2005 | Matsumoto | H01J 37/32174 257/E21.252 |
| 2008/0099437 A1 | 5/2008 | Lewington et al. | |
| 2009/0029489 A1 | 1/2009 | Park et al. | |
| 2013/0087098 A1 | 4/2013 | Finarov | |
| 2016/0033328 A1* | 2/2016 | Walters | G01J 3/0289 356/326 |
| 2018/0286768 A1 | 4/2018 | Woodard et al. | |

* cited by examiner

LOW OPEN AREA AND COUPON ENDPOINT DETECTION

TECHNICAL FIELD

Embodiments of the disclosure relate, generally, to detecting an endpoint in plasma-assisted wafer processing step in a chamber; and, specifically to detecting endpoint by analyzing high-resolution and high-selectivity spectrographic signatures of various chemical species during plasma-assisted wafer processing step(s) in a recipe, especially, when the processed wafer (or coupon) has a low open area.

BACKGROUND

Semiconductor wafers contain many materials deposited, etched, and/or patterned in several layers. A wafer processing recipe may comprise one or more steps involving creation of a plasma inside a chamber (also referred to as processing chamber or reactor) that assists in the addition or removal of a layer or patterning a layer. A plasma is a superposition of many different chemical species having corresponding wavelengths resulting from transition of a particle from an excited state to a ground state. When a photodetector's processing circuitry analyzes those wavelengths, the identity of the chemical species can be detected. Based on the prior knowledge of what chemical species are expected to be associated with a particular stage of wafer processing, spectrographic signatures, specific composition changes in the plasma, can be useful tools for determining whether an endpoint has been reached for a particular process or process step.

Detectability of spectrographic signature depends significantly on optical signal strength of key emission spectral lines. When plasma can reach an open area of wide dimension, then optical emission generated from many atoms or molecules of a chemical species is collected and optical signal strength increases; however, when a small portion of a wafer, such as a coupon is processed—often during a process development stage, e.g. during design of experiments (DoE), chamber calibration or process parameter tuning—the signal strength is low, as the source of the signal is very few excited atoms or molecules coming from the coupon. Even if a bigger portion of the wafer or a whole wafer is being processed, if the wafer contains certain device features that have very "low" open areas, then the same problem of low signal strength is encountered. As a non-limiting, illustrative example: during etching of a high aspect ratio (HAR) deep structure (e.g. a memory hole), it might be difficult to get optical signal of adequate strength from the bottom of the deep structure as very few atoms or molecules are accessed from all the way into the depth of the structure.

A reliable endpoint detection solution, even when the chemical species to be detected is from an open area that is less than 10% of the wafer area, and/or when one or a few coupons are processed rather than a processing a full wafer or a larger portion of a wafer with wider open areas is needed to address these problems.

Echelle style spectrometers offer high spectral resolution; however, they are very costly and the signal-to-noise ratio (SNR) is not satisfactory. Echelle spectrometers may be suitable for emission line identification during research and development; but, not as a product catering to high yield mass production of wafers. This disclosure describes a novel spectrographic detector with very high bandwidth, and very high selectivity suitable to high volume manufacturing of wafers, as described below.

SUMMARY

The following is a simplified summary of the disclosure in order to provide a basic understanding of some aspects of the disclosure. This summary is not an extensive overview of the disclosure. It is intended to neither identify key or critical elements of the disclosure, nor delineate any scope of the particular implementations of the disclosure or any scope of the claims. Its sole purpose is to present some concepts of the disclosure in a simplified form as a prelude to the more detailed description that is presented later.

The disclosure describes techniques and apparatuses for detecting an endpoint in plasma-assisted wafer processing in a chamber, which may be especially beneficial when using one or more coupons or wafers with devices having low open areas that present a challenge in getting adequate signal strength to detect chemical species involved in the plasma process. The apparatuses comprise ultra-narrow bandwidth filters coupled to photon detection electronics including, but not limited to photomultiplier tube (PMT) arrays (sometimes referred to as pixelated arrays), or, a plurality of photodiodes with corresponding ultra-narrow bandwidth filters. Available light emitted during a plasma process inside a processing chamber is collected and collimated using a fiber bundle and carried to the PMT array or the photodiodes. The endpoint of a certain process recipe or recipe step is detected based on detecting presence or absence of certain chemical species indicated in the spectrographic signature of the collected light. The disclosed detectors are low cost, high gain, and customized filters tailored to the expected wavelength of emitted light from specific species in the chamber during a plasma-assisted process provides high selectivity.

More specifically, in one aspect of the present disclosure, an apparatus (and corresponding method) for detecting an endpoint in plasma-assisted wafer processing in a chamber is disclosed. The apparatus comprises: a fiber array comprising a plurality of fibers collecting optical emission light from the chamber during the plasma-assisted wafer processing, wherein the plurality of fibers is split into two or more groups of fibers, each group of fibers carrying a portion of the optical emission light as a respective optical signal; a photodetector having a plurality of segments, each segment having a corresponding narrowband optical filter designed for a specific range of wavelengths, wherein one or more ranges of wavelengths are indicative of a presence or an absence of one or more chemical species associated with the plasma-assisted wafer-processing in the chamber, and wherein each group of fibers couples the respective optical signal with a corresponding segment of the photodetector; and, a computer processor, that analyzes detected signals from the plurality of segments of the photodetector, and determines, based on the analysis of the detected signals, an endpoint of the plasma-assisted wafer processing as indicated by the presence or the absence of the one or more chemical species in the chamber.

BRIEF DESCRIPTION OF THE DRAWINGS

The present disclosure will be understood more fully from the detailed description given below and from the accompanying drawings of various embodiments of the disclosure.

DETAILED DESCRIPTION

Embodiments of the present disclosure are directed to a custom filter assembly coupled to either a PMT array or a plurality of photodiodes, for high-selectivity detection of chemical species using spectrographic methods. The presence or absence of certain chemical species in the spectrographic signal is indicative of an endpoint of a certain plasma process or step of a plasma process in a wafer processing recipe.

As described above, endpoint detection is particularly challenging when the open area from which optical signal collected for spectrographic analysis is low (e.g. 1-10% of the total exposed area of the wafer is involved in producing the species of interest). Similar challenges are encountered for coupons also because of the small areas of the coupons. Though Echelle style spectrometers provide very high spectral resolution, they suffer from low signal-to-noise ratio (SNR) and are prohibitively costly. So even if Echelle-style spectrometers are good candidates during research and development stage, they are not suitable for mass production.

Aspects of the present disclosure address this and other limitations by 'pixelated' PMT array or photodiodes. "Pixelated" in the present context means respective areas of the PMT array or respective photodiodes in a plurality of photodiodes are assigned to corresponding respective narrow range of bandwidths by using suitable wavelength filters. While PMTs or photodiodes (including, Avalanche Photodiodes (APDs), which are a particular type of photodiodes with high reverse bias) provide high enough gain to amplify weak optical signals, the ultra-narrow bandwidth filters provide wavelength selectivity, which leads to high selectivity in detecting the presence of absence of a corresponding chemical species. Both the PMT-based configuration and the photodiode-based configuration are suitable for mass production because of high performance at a relatively low cost. Additional advantages include, but are not limited to, possibility of customization of the configuration based on a particular recipe step in the plasma-assisted wafer processing flow, as described with respect to FIG. 1.

Figure 1:
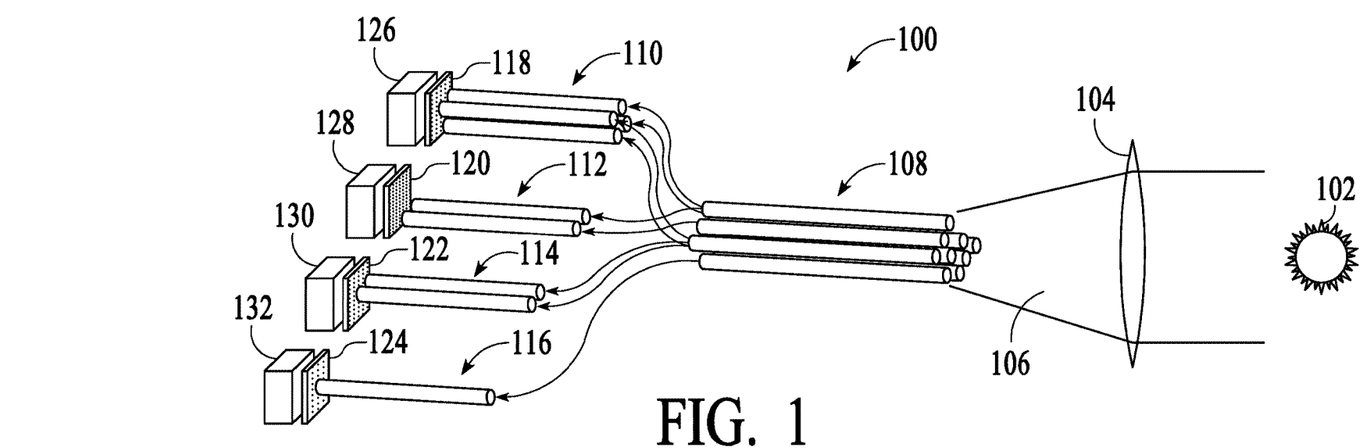
FIG. 1 illustrates a photodetector configuration comprising a plurality of photodiodes each having a respective wavelength filter, according to a first embodiment of the present disclosure.

FIG. 1 illustrates a photodetector configuration 100 comprising a plurality of photodiodes (PDs) (which can be, but does not have to be, avalanche photodiodes (APDs)), each having a respective wavelength filter, according to a first embodiment of the present disclosure. Optical emission 102 from a plasma within a processing chamber is collected and is collimated by a lens 104 into an input beam 106 that is collected by a fiber bundle 108. The fiber bundle 108 comprises a plurality of individual fiber optic cables (FOCs) (sometimes simply called 'fibers'). The fiber bundle has the advantage of being less cumbersome, as there are not many additional optical elements (i.e. slits, diffraction elements etc.) in between the processing chamber and the photodetectors.

The fiber bundle 108 can be split into two or more groups of fibers. For example, in FIG. 1, the fiber bundle 108 is split into four groups 110, 112, 114 and 116. Note that any other number of groups is possible depending on the number of photodiodes to which the beam 106 is transported to. Number of individual fibers in each group does not have to be the same. In fact, the ability to change the number of individual fibers in each group is a key aspect of customization that embodiments of the present disclosure offer. Increasing or decreasing the number of fibers in each group helps in increasing or decreasing total optical signal intensity that is being coupled to the respective filters 118, 120, 122 and 124 corresponding to the photodiodes 126, 128, 130 and 132 respectively. The photodiodes may be APDs to provide high gain to boost optical signal intensity for the filtered wavelength.

Each of the filters 118, 120, 122 and 124 is designed to have ultra-narrow bandwidth, letting only a very narrow range of wavelength to pass to the photodiodes, while blocking off other wavelengths outside of the designed range. For example, filter 118 may be optimized for a center wavelength $\lambda 1$, filter 120 may be optimized for a center wavelength $\lambda 2$, filter 122 may be optimized for a center wavelength $\lambda 3$, and filter 118 may be optimized for a center wavelength $\lambda 4$. Each of the filters may have a 0.1-4.0 nm full width half max (FWHM) around a center wavelength. The optical density (OD) of the filters are typically greater or equal to 4, i.e. filters may be of OD4 or higher. This means that the OD outside the bandpass region, also referred to 'out of band region,' may be customized depending on application and sensor type, but typically vary from OD=4 and can have a higher value (e.g., a non-limiting example is OD=6).

The wavelengths are indicative of the chemical species that is creating at least part of the plasma in the processing chamber, and therefore bear the spectral signature of that chemical species. For example, tungsten (also known as wolfram, chemical symbol W) has an emission peak at a wavelength that is very different from the emission peak wavelength for silicon (Si). Moreover, even one chemical species (e.g., silicon) can show multiple emission peaks at different wavelengths based on the variation in relaxation energy. These will be described in greater detail with respect to FIG. 7.

Note that as an initial step for designing the narrow bandwidth filters 118, 120, 122 and 124, key emission lines for a plasma-assisted wafer processing (or a step of a recipe) may be identified using a high-resolution broadband spectrometer, recognizing that different steps of the recipe give out different emission spectra, as different combination of chemical species are involved in creating the emission spectra. Once a current process step comes to an end, there may be a marked change in the emission spectra, as certain emission peaks may disappear and/or certain new emission peaks may become prominent. The spectrographic signature is directly correlated with the progress of a process step. For example, for a tungsten-covered silicon wafer, when the tungsten layer is completely etched through, then underlying silicon becomes exposed and the Si emission peaks become prominent while the tungsten emission peak disappears.

Figure 2:
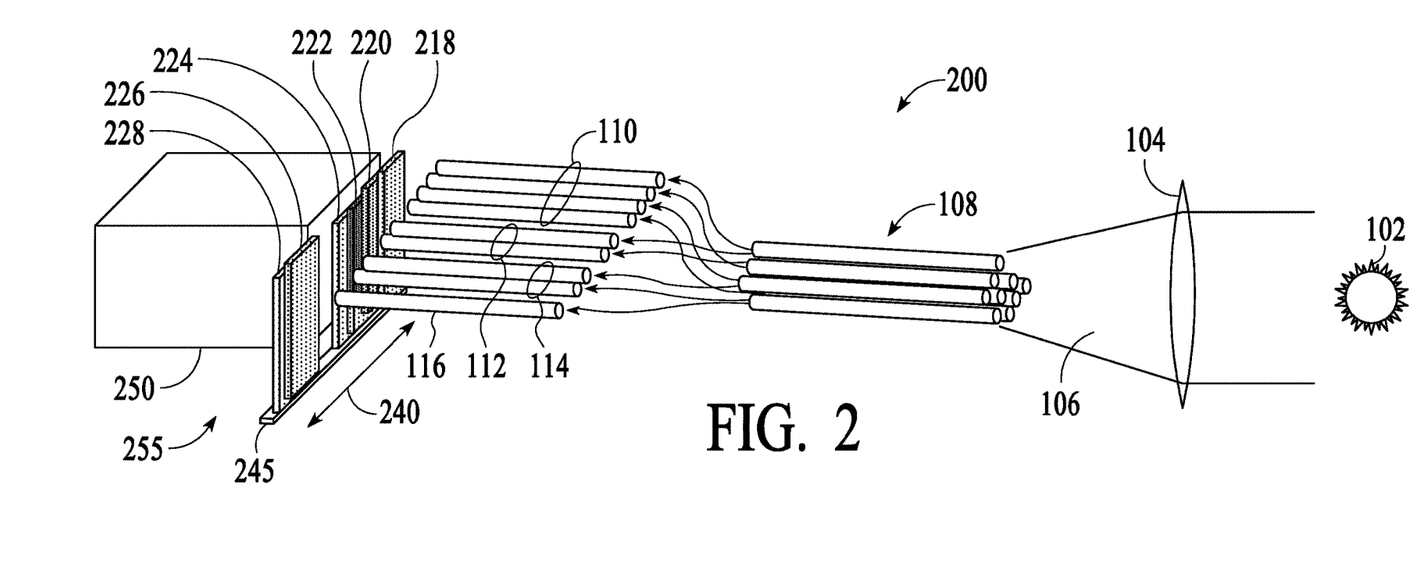
FIG. 2 illustrates a photodetector configuration comprising a plurality of photomuliplier tubes (PMTs) with a linear array of wavelength filters, according to a second embodiment of the present disclosure.

FIG. 2 illustrates a photodetector configuration 200 comprising a plurality of photomultiplier tubes (PMTs) with an array of wavelength filters, according to a second embodiment of the present disclosure. This configuration also includes the same source of the optical emission 102 (i.e. the plasma within a chamber), lens 104 and collimated beam 106 leading to the fiber bundle 108. A key difference of this configuration with the photodiode-based configuration shown in FIG. 1 is that a filter assembly 255 is mounted movably in front of a detector housing referred to as a PMT assembly 250. The PMT assembly 250 comprises an array of photomultiplier tubes, which is often referred to as PMT array. The PMT array can be thought of a multi-anode PMT assembly, where there are multiple photomultiplier anodes. In a non-limiting example, a PMT array can have 16 anodes. Note that depending on the arrangement of the photomultiplier anodes in the PMT assembly 250, the filter assembly 255 may be moved in a linear motion (as shown in the example in FIG. 2) or may be may be mounted on a circular wheel and is rotated to place the desired filter assembly in front of the multianode PMT. In case of a linear arrangement 255, the individual filters may be mounted on a slider 245 which slides back and forth along the direction of the double-headed arrow 240 parallel to a front surface of the PMT assembly 250. In case of a circular arrangement, the filter assembly may be mounted on a rotary wheel in front of the PMT assembly 250. The PMT assembly may have 'n' number of channels with minimum crosstalk between the channels. Each channel does not necessarily have to process signal from equal number of photomultiplier tubes.

Referring back to the example of linear array of filters, each of the filters 218, 220, 222, 224, 226 and 228 may be designed for certain narrow wavelength range. Each of the filters may have FWHM of 0.1-0.4 nm and may be characterized as OD4 or higher, i.e. may have oou-of-band rejection of 4 or higher. The fiber bundle 108 is split into four groups 110, 112, 114 and 116, which may also be linearly arrayed as shown in FIG. 2. The mutually-aligned arrangement of the filter assembly 255 and the front surface of the PMT assembly 250 is elaborated with respect to FIGS. 3 and 4 below.

Figure 3:
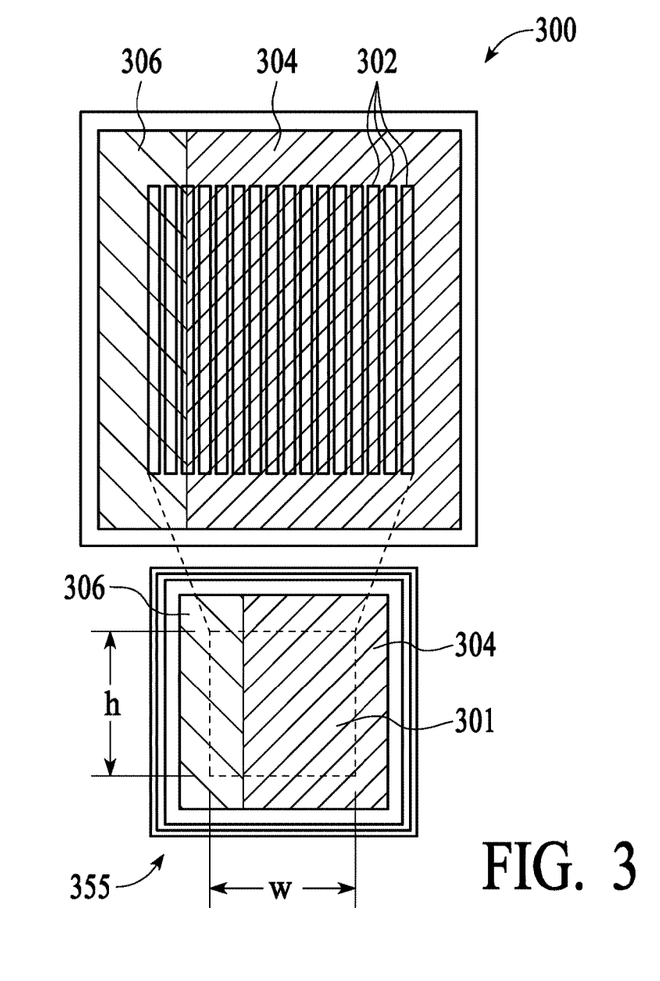
FIG. 3 illustrates a front view of a PMT array which detects a reference wavelength and one additional wavelength, according to an embodiment of the present disclosure.

FIG. 3 illustrates a front view of a PMT array which detects a reference wavelength and one additional wavelength, according to an embodiment of the present disclosure. PMTs demonstrate excellent optical gain, large dynamic range and good signal-to-noise ratio. Specifically, the upper figure in FIG. 3 shows a PMT array 300 with a reference wavelength detection region (pixel 306) and a bigger region (pixel 304) detecting the additional wavelength. The lower figure of FIG. 3 shows the relative dimension of an entire PMT multianode region 301 (bounded by the dashed rectangle) of a detector 355. The PMT multianode region 301 has a height of 'h' and width of 'w'. A plurality of photomultiplier anodes 302 within the PMT array 300 are aligned with the PMT multianode region 301 of the detector 355, and the slider 245 of the filter assembly 255 (shown in FIG. 2) aligns appropriate wavelength-selective filters (218, 220, 222, 224, 226, 228) with respect to the PMT array 300.

Figure 4:
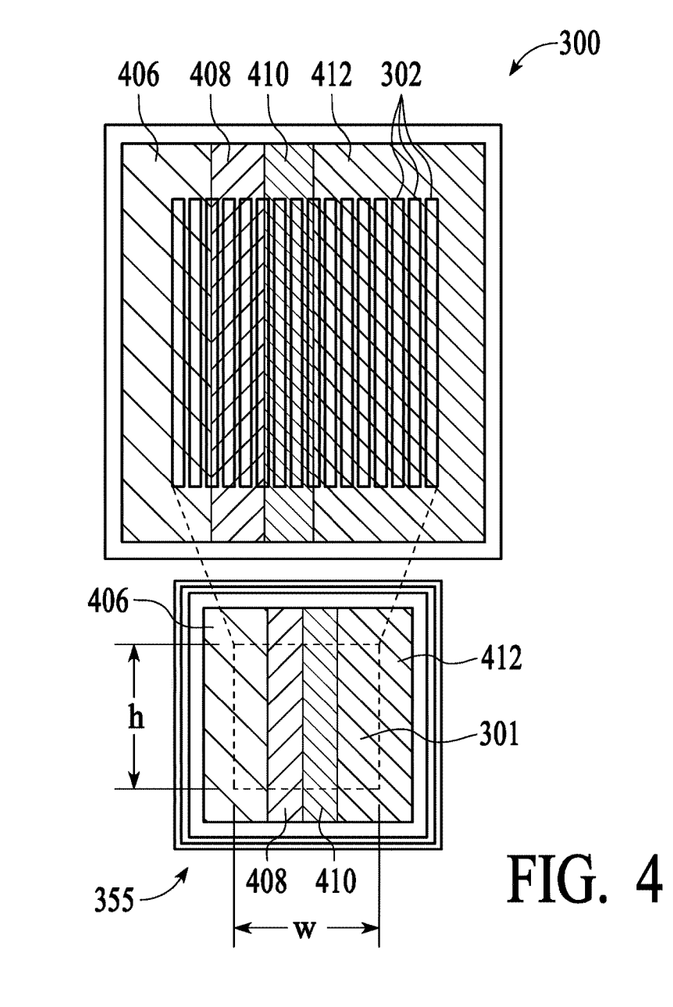
FIG. 4 illustrates a front view of a PMT array which detects a reference wavelength and three additional wavelengths, even if the optical signal strength of one of the additional wavelengths is relatively weak, according to an embodiment of the present disclosure.

FIG. 4 illustrates a front view of the same PMT array 300 which, with appropriate wavelength filters, can detect a reference wavelength and three additional wavelengths, even if the optical signal strength of one of the additional wavelengths is relatively weak, according to an embodiment of the present disclosure. Specifically, the upper figure in FIG. 4 shows a PMT array 300 with a reference wavelength detection region (pixel 406) and a three other regions (pixels 408, 410 and 412) detecting three additional wavelength ranges. The lower figure of FIG. 4 shows the relative dimension of an entire PMT multianode region 301 with a height of 'h' and width of 'w', similar to FIG. 3. The reference wavelength detected by pixel 306 in FIG. 3 and pixel 406 in FIG. 4 may be the same, and the physical dimension of pixels 306 and 406 may be same or similar. Relative physical dimensions of the other pixels in the photodetector 355 may vary depending on expected relative strengths of respective optical signals carried by the respective groups of fibers. For example, the optical signal strength of emission peak in the wavelength range detected by pixel 412 may be much lower than the optical signal strength of emission peak in the wavelength range detected by pixel 408 or 410. Therefore, are of pixel 412 is larger than the areas of pixels 408 and 410. As will be appreciated, in view of the present disclosure, number of fibers carrying the low-strength optical signal to pixel 412 is likely to be higher than the number of fibers carrying the relatively high-strength optical signals to pixels 408 and 410. This ability to customize the split of the fiber bundle 108 is one of the unique features of the present disclosure.

Figure 5:
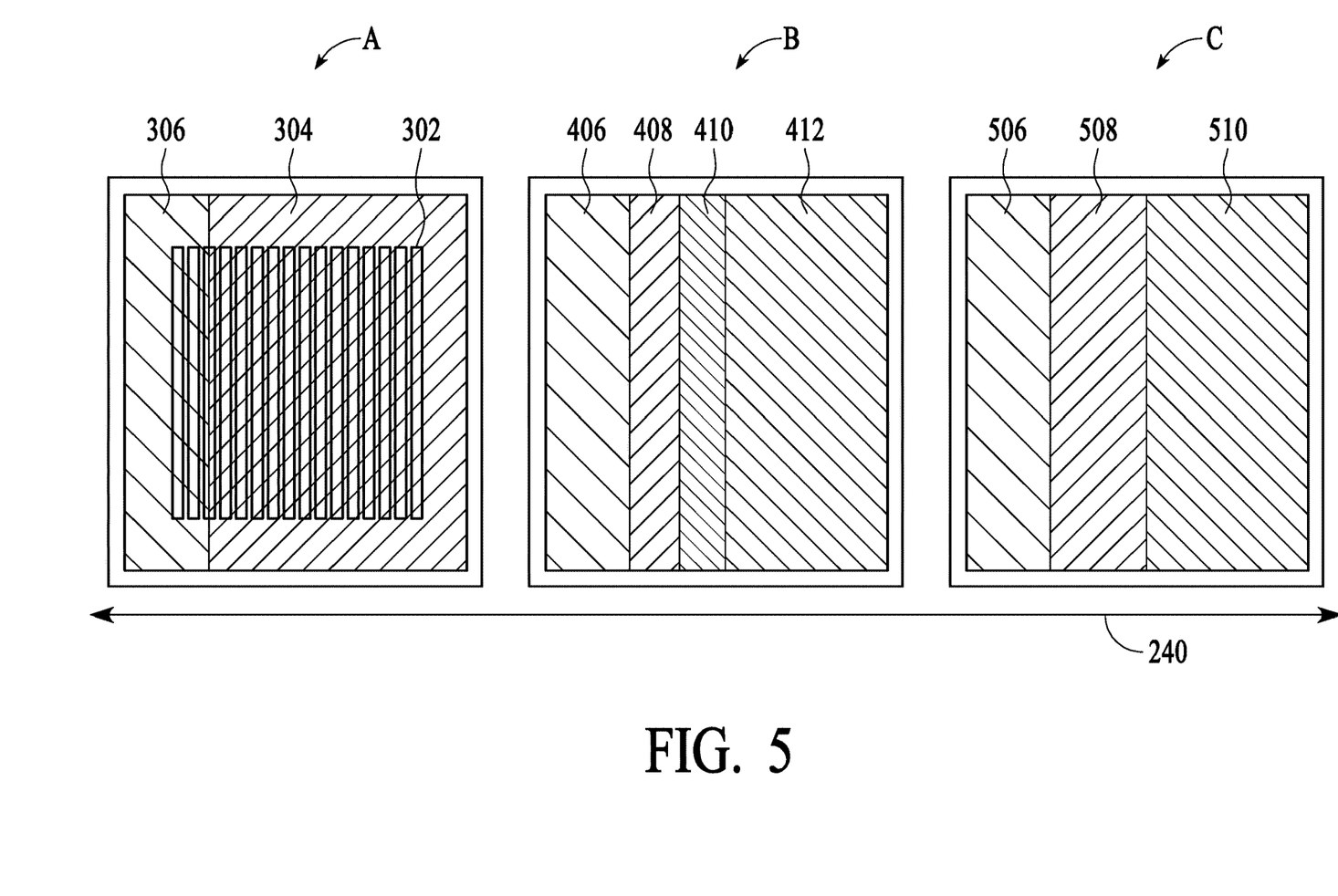
FIG. 5 illustrates how a filter assembly with a linear array of wavelength filters can be laterally moved to align with the PMT array depending on which chemical species is expected to be detected at a certain stage of the wafer processing, according to an embodiment of the present disclosure.

FIG. 5 illustrates how a filter assembly with a linear array of wavelength filters can be laterally moved to align with the PMT array depending on which chemical species are expected to be detected at a certain stage of the wafer processing, according to an embodiment of the present disclosure. For example, the left figure (filter combination 'A') shows a reference wavelength region (pixel 306) and one additional pixel 304, when it is expected that only one emission peak at a certain wavelength range is to be detected. The middle figure (filter combination 'B') shows a reference wavelength region (pixel 406) and three additional pixels 408, 410 and 412, when it is expected that three prominent emission peaks at three wavelength ranges are to be detected. Similarly, the right figure (filter combination 'C') shows a reference wavelength region (pixel 506) and two additional pixels 508 and 510, when it is expected that two prominent emission peaks at two wavelength ranges are to be detected. The combination of emission peaks may indicate which stage a certain process is currently at, and the appearance or disappearance of certain emission peaks, or increased or decreased prominence of certain emission peaks at certain temporal points may indicate reaching an endpoint. The filter array 255 may use a reference filter for DC level subtraction from the signal detected in pixels 306, 406 or 506. The double-headed arrow 240 (shown in FIG. 2 also) indicates that using the slider 245, any combination of filters (e.g., combinations shown in 'A', 'B' or 'C') can be aligned with the multianode PMT 302. In other words, FIG. 5 shows that the PMTs are currently aligned with filter combination 'A' for a certain recipe step. But when the recipe step changes, the PMTs may be aligned with filter combination 'B', and when the recipe step changes further, the PMTs may be aligned with filter combination 'C' and so on.

Figure 6:
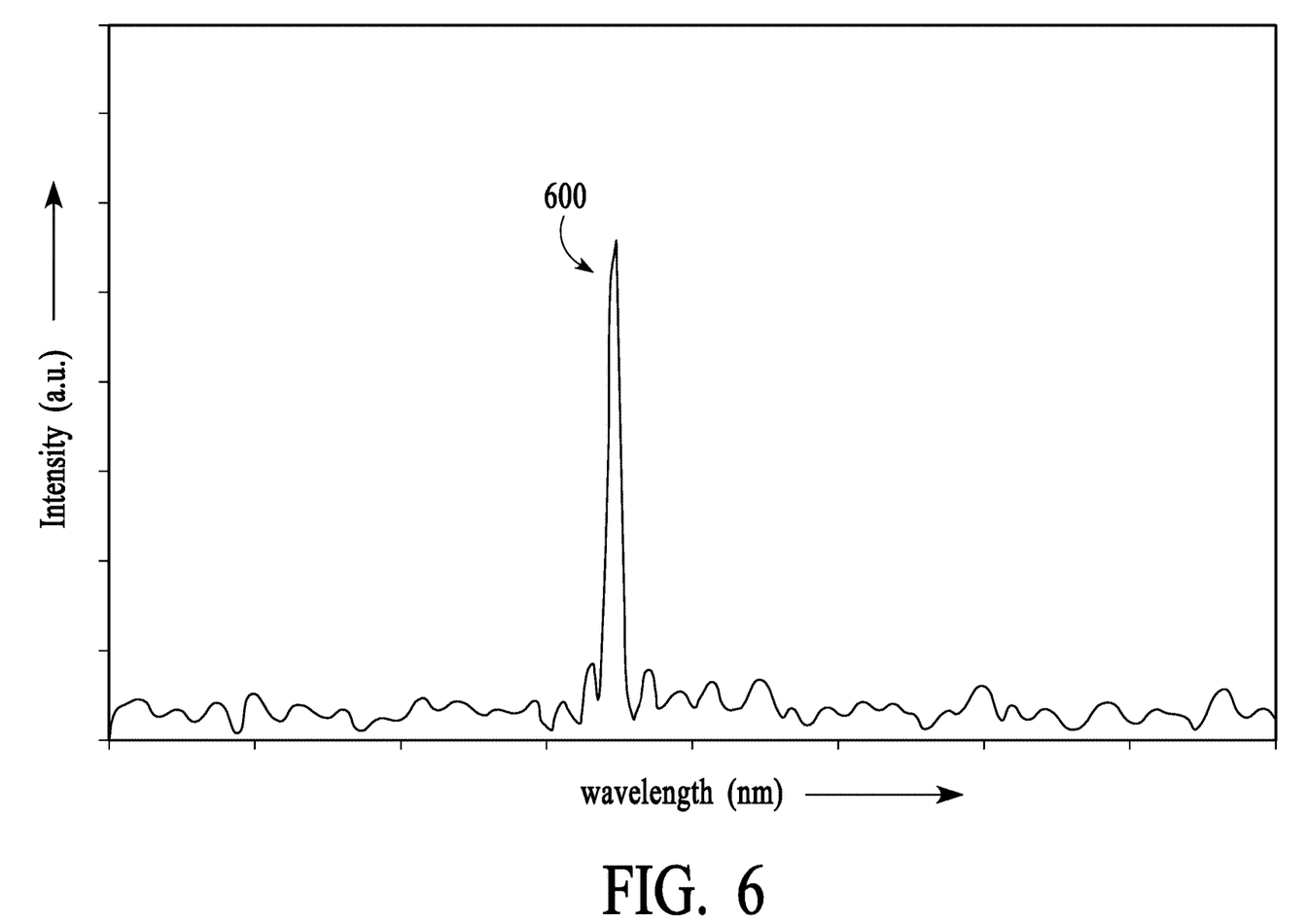
FIG. 6 illustrates a plot showing one prominent peak for a dominant chemical species indicating a processing stage of a certain plasma process, according to an embodiment of the present disclosure.

FIG. 6 illustrates a plot showing one prominent peak for a dominant chemical species indicating a certain stage of a certain plasma process, according to an embodiment of the present disclosure. As a non-limiting example, the prominent peak 600 at a certain wavelength may indicate that the plasma inside the processing chamber contains a certain metal or other chemical species. When the entire layer of that metal (or the other chemical species) is etched away (or is covered with certain other material), then this prominent peak 600 may disappear and/or other prominent peaks may emerge.

Figure 7:
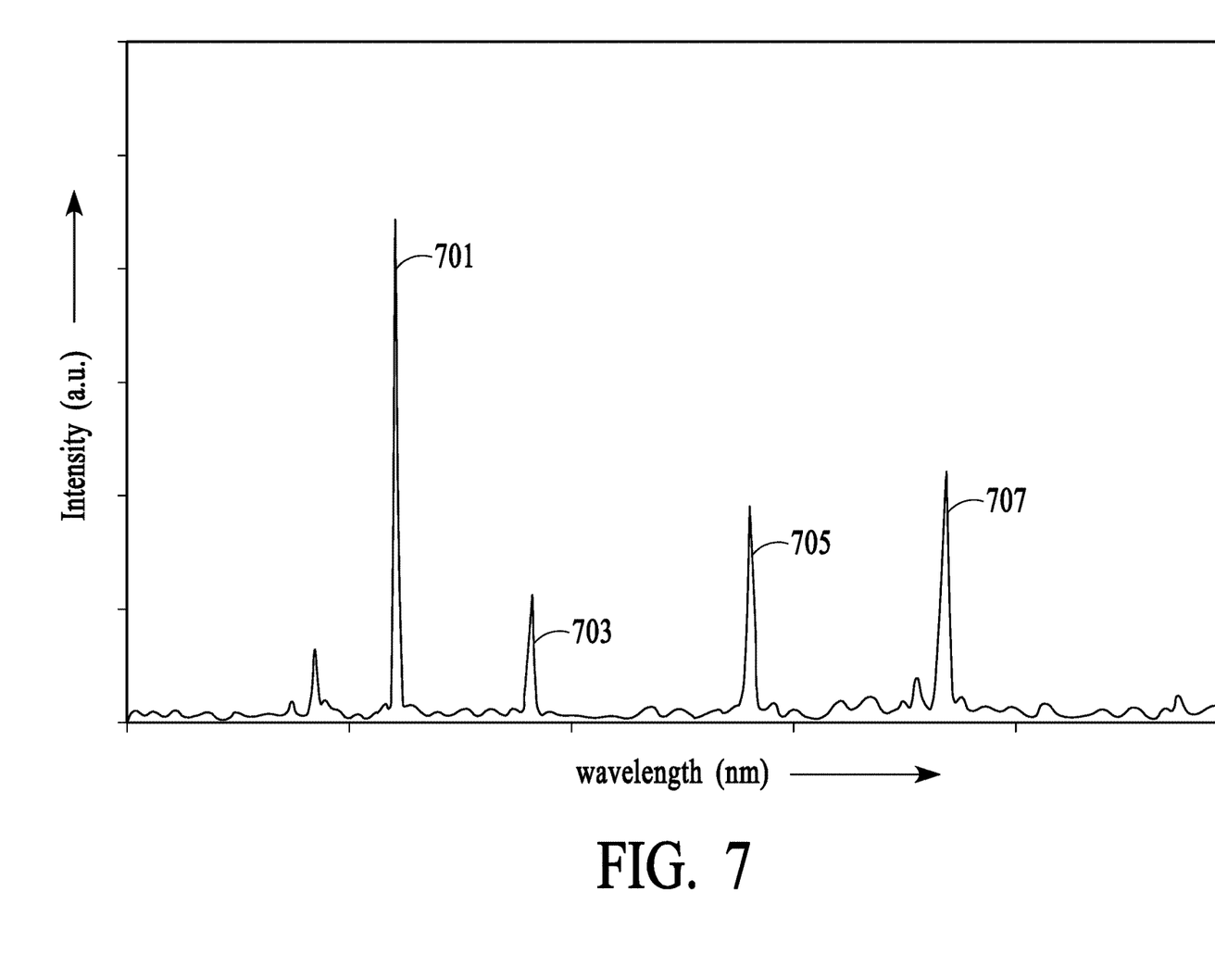
FIG. 7 illustrates a portion of spectra coming from multiple chemical species in a processing chamber, from which a most prominent peak is isolated from adjacent sub-peaks in order to achieve high species selectivity by proper filter design, according to an embodiment of the present disclosure.

FIG. 7 shows a portion of the spectra coming from a combination of potential endpoint species (701) and other chemical species (703, 705, 707). The high resolution of a traditional high-resolution spectrometer, such as an echelle spectrometer, allows for the clear observation of these peaks. This, in turn, guides the design of the ultra-narrow bandwidth filters of this disclosure so only the species of interest (701) is collected by the photodiodes or PMTs described in FIGS. 1 and 2 respectively. Thus, high species-selectivity is achieved at a lower cost and simpler design described in this disclosure.

Figure 8:
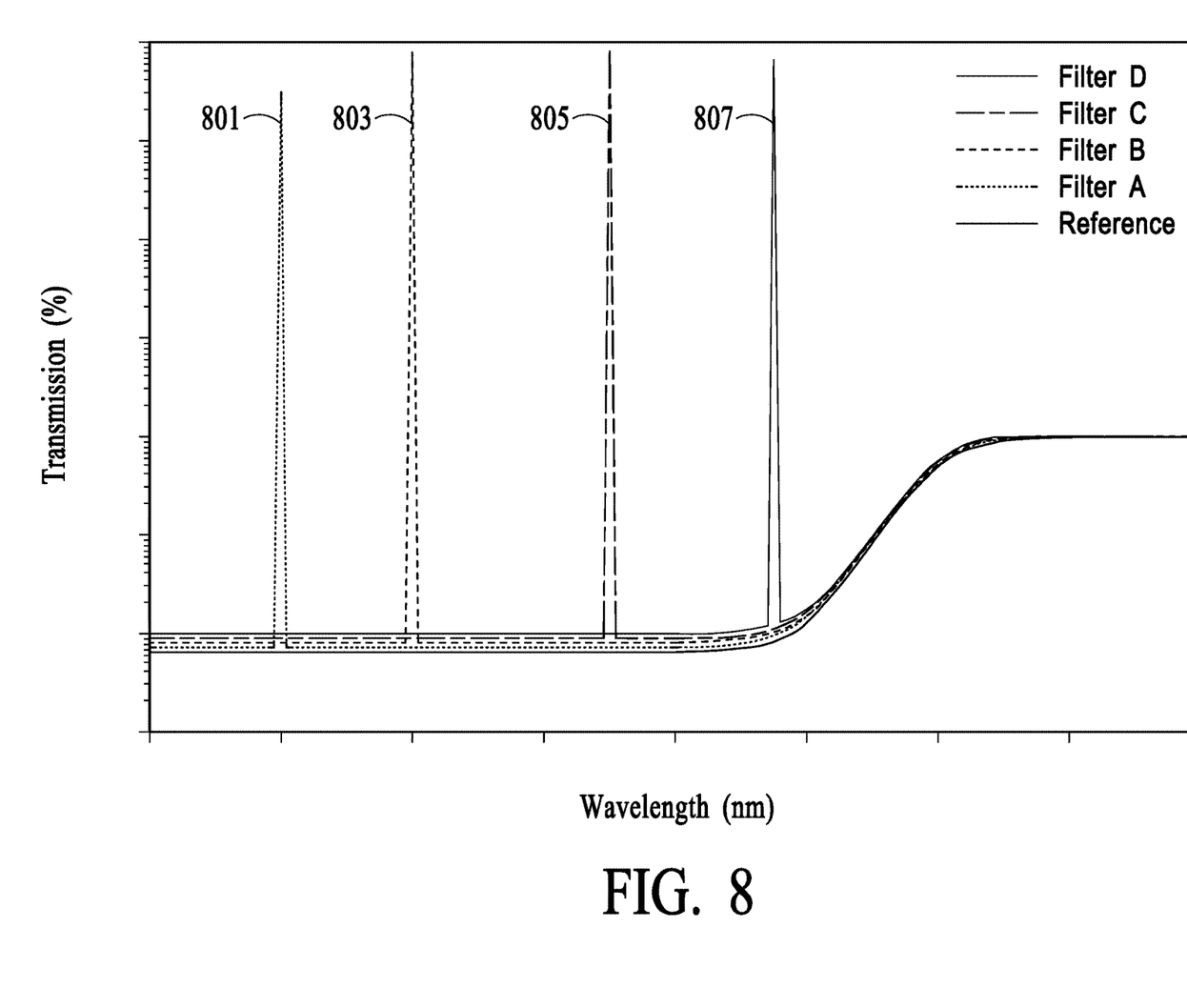
FIG. 8 illustrates results of an experiment with various filter designs, according to an embodiment of the present disclosure.

FIG. 8 illustrates results of an experiment with various filter designs, according to an embodiment of the present disclosure. The curves 801, 803, 805 and 807 shown with different line patterns correspond to specific filter designs (referred to as Filter A, Filter B, Filter C and Filter D respectively), optimized for filtering the emission peaks within certain narrow wavelength ranges. The bottom-most curve with no peak shown with a solid line corresponds to a reference signal with respect to which differential measurements are performed for each of the filter designs. The goal of a reference signal is to match all of the out-of-band transmission in any of the other customized filter designs, so that the reference signal can be subtracted from each of the customized filter designs, and only a prominent signal in the wavelength range of interest is obtained. Note that the curves 801, 803, 805 and 807 are shown to have slight vertical offset (along Y axis) at the base just for illustrative clarity. The curves are not necessarily drawn to scale and are merely provided to convey the concept of wavelength-specific filter design using a reference signal.

Figure 9:
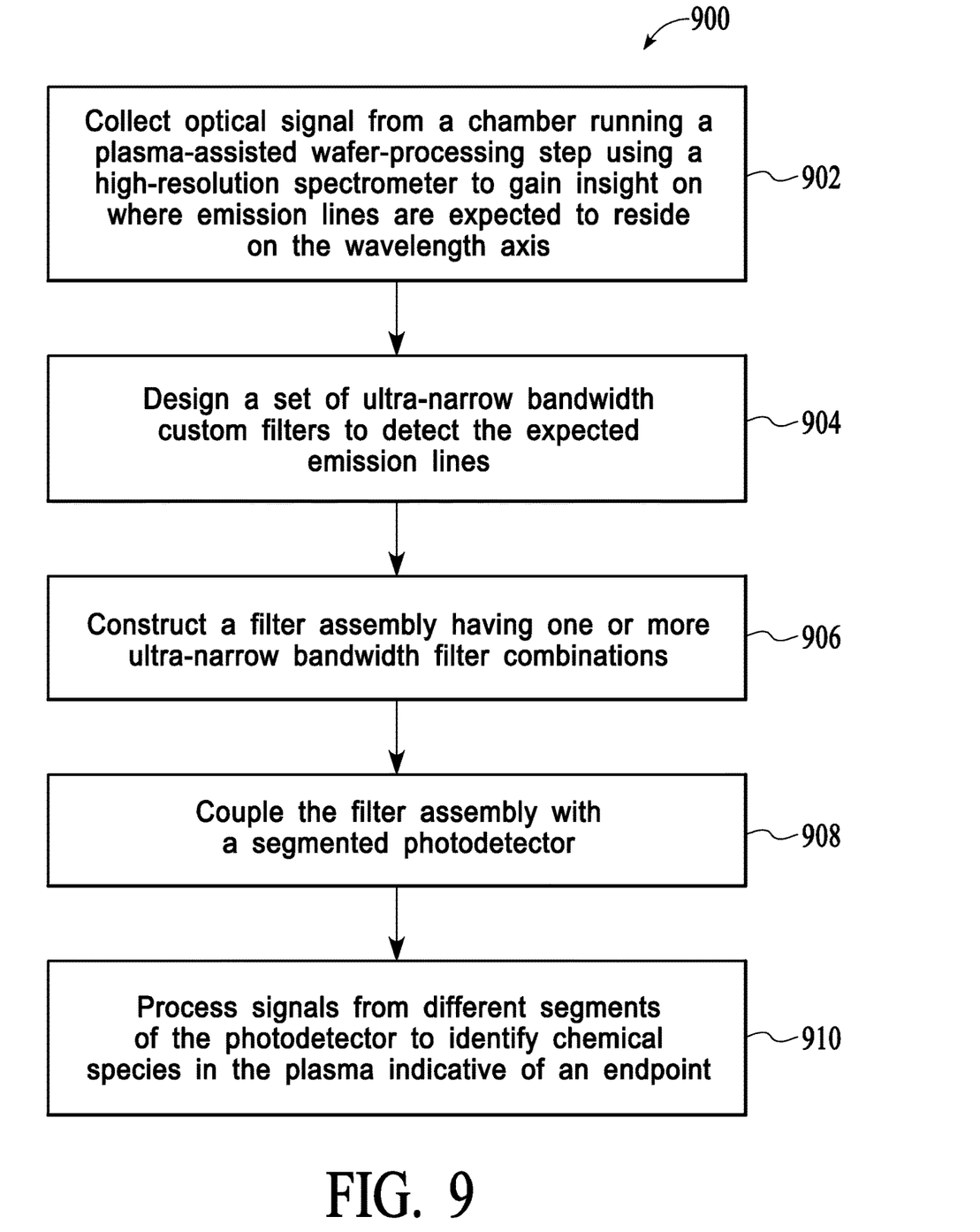
FIG. 9 is a flow chart showing a process for endpoint detection, in accordance with embodiments of the present disclosure.

FIG. 9 is a flow diagram of an example method 900 to of endpoint detection, in accordance with some embodiments of the present disclosure. The method 900 can be performed by at least partially by processing logic that can include hardware (e.g., processing device, circuitry, dedicated logic, programmable logic, microcode, hardware of a device, integrated circuit, etc.), software (e.g., instructions run or executed on a processing device), or a combination thereof. The processing logic portion is part of a photodetector (i.e. electrically coupled to the PMT array, as shown in FIG. 2, or the plurality of photodiodes, such as APDs or other types of diodes, as shown in FIG. 1). Although shown in a particular sequence or order, unless otherwise specified, the order of the processes in method 900 or other methods described below with illustrative flowcharts can be modified. Thus, the illustrated embodiments should be understood only as examples, and the illustrated processes can be performed in a different order, and some processes can be performed in parallel. Additionally, one or more processes can be omitted in various embodiments. Thus, not all processes are required in every embodiment. Other process flows are possible.

At block 902, optical signal is collected from a chamber running a plasma-assisted wafer processing step. Before designing the custom filters, this data can be collected with a high-resolution spectrometer (typically resolution lower than 1 nm) in order to have an idea of where the emission lines (peaks of the emission spectra) would reside for particular process steps.

At block 904, a set of custom filters is designed, each filter having an ultra-narrow bandwidth (e.g., ~0.1 nm to 4 nm FWHM and OD4-OD6 out of band rejection) for the emission lines of interest.

At block 906, one or more filter assemblies are constructed, the filter assembly containing one or more filter combinations. Each of the filter combinations in the filter assembly has a reference filter and at least one other narrowband filter. The emission lines of interest for endpointing may be different for different recipes and different processing steps. Accordingly, the filter combinations can be automatically changed based on the chosen recipe and between different processing steps within a recipe. This can be accomplished via a linear slide or a rotary wheel depending on the geometric arrangement of the filter combinations.

At block 908, the filter assembly is coupled to a photodetector with multiple segments. The photodetector may be a PMT array. In case of other configurations of segmented photodetector, e.g., APDs constituting each segment, each APD can have its own filter, rather than having a filter combination.

At block 910, the detected signal from the photodetector is processed. A custom trans-impedance amplifier and a summing circuit may be used to remove out-of-band signal from the primary signal to further improve the dynamic range and SNR. A background removal step may be available to accommodate plasma light level changes from recipe to recipe and from one step to another step. Custom algorithms are used to detect the appearance and disappearance of signal from different channels of a PMT array to endpoint a given recipe step.

In the foregoing specification, implementations of the disclosure have been described with reference to specific example implementations thereof. It will be evident that various modifications can be made thereto without departing from the broader spirit and scope of implementations of the disclosure as set forth in the following claims. The specification and drawings are, accordingly, to be regarded in an illustrative sense rather than a restrictive sense.

What is claimed is:

1. An apparatus for detecting an endpoint in plasma-assisted wafer processing in a chamber, the apparatus comprising:
a fiber array comprising a plurality of fibers collecting optical emission light from the chamber during the plasma-assisted wafer processing, wherein the plurality of fibers is split into two or more groups of fibers, each group of fibers carrying a portion of the optical emission light as a respective optical signal, each group of fibers being a discrete bundle of fibers, each discrete bundle of fibers being separated from at least one other discrete bundle of fibers;
a photodetector having a plurality of segments, each segment having a corresponding narrowband optical filter designed for a specific range of wavelengths, wherein one or more ranges of wavelengths are indicative of a presence or an absence of one or more chemical species associated with the plasma-assisted wafer processing in the chamber, and wherein each group of fibers couples the respective optical signal with a corresponding segment of the photodetector; and a computer processor, that analyzes detected signals from the plurality of segments of the photodetector, and determines, based on analysis of the detected signals, an endpoint of the plasma-assisted wafer processing as indicated by the presence or the absence of the one or more chemical species in the chamber.

2. The apparatus of claim 1, wherein a specimen being processed in the chamber during the plasma-assisted wafer processing comprises one or more coupons.

3. The apparatus of claim 1, wherein a specimen being processed in the chamber during the plasma-assisted wafer processing comprises a wafer or a portion thereof having one or more device features with a low open area.

4. The apparatus of claim 1, wherein each narrowband optical filter has a full width half maximum (FWHM) value of 0.1-4.0 nm.

5. The apparatus of claim 1, wherein each narrowband optical filter has an out-of-band rejection parameter represented by optical density (OD) value of OD4 or higher.

6. The apparatus of claim 1, wherein the photodetector comprises a plurality of photomultiplier tube (PMT) anodes, wherein each segment comprises one or more anodes.

7. The apparatus of claim 1, wherein a plurality of narrowband optical filters is assembled in the form of an array.

8. The apparatus of claim 7, wherein a physical dimensions of the narrowband optical filters assembled in the array varies depending on expected relative strengths of respective optical signals carried by the respective group of fibers coupled to the respective narrowband optical filters.

9. The apparatus of claim 7, wherein the array includes a reference filter for DC level subtraction.

10. The apparatus of claim 7, wherein the array is mounted movably with respect to the photodetector such that an alignment of a particular narrowband filter with respect to a segment of the photodetector can be changed.

11. The apparatus of claim 10, wherein the array is a linear array and is mounted on a slider to move laterally with respect to the photodetector.

12. The apparatus of claim 10, wherein the array is a radial array and is mounted on a rotary wheel to move rotationally with respect to the photodetector.

13. The apparatus of claim 1, wherein each segment of the photodetector comprises a photodiode.

14. The apparatus of claim 13, wherein each photodiode has a corresponding narrowband optical filter.

15. The apparatus of claim 1, wherein number of fibers in each discrete bundle of fibers is not identical.

16. The apparatus of claim 1, wherein the endpoint in the plasma-assisted wafer processing indicates termination of a particular step in a process recipe, wherein the particular step is characterized by the presence or an absence of one or more specific chemical species.

* * * * *